(12) United States Patent
Tamura

(10) Patent No.: US 6,814,701 B1
(45) Date of Patent: Nov. 9, 2004

(54) METHOD AND APPARATUS FOR ULTRASOUND DIAGNOSTIC IMAGING

(75) Inventor: Tadashi Tamura, North Haven, CT (US)

(73) Assignee: Aloka Co., Ltd. (JP)

( * ) Notice: Subject to any disclaimer, the term of this patent is extended or adjusted under 35 U.S.C. 154(b) by 10 days.

(21) Appl. No.: 10/414,888

(22) Filed: Apr. 16, 2003

(51) Int. Cl.$^7$ ................................................ A61B 8/00
(52) U.S. Cl. ..................................................... 600/443
(58) Field of Search .............................. 600/437–472, 600/595; 73/625, 626–633; 367/7, 11, 88, 130, 138; 128/916

(56) References Cited

U.S. PATENT DOCUMENTS 5,573,012 A * 11/1996 McEwan .................... 600/595
5,766,208 A * 6/1998 McEwan .................... 600/595
6,438,071 B1 * 8/2002 Hansen et al. ................ 367/88

* cited by examiner

Primary Examiner—Ali Imam
(74) Attorney, Agent, or Firm—Bachman & LaPointe, P.C.

(57) ABSTRACT

In accordance with the present invention, a method for reducing noise in ultrasound images comprising the steps of transmitting and receiving from an ultrasound transducer comprising a plurality of apexes a plurality of ultrasound beams from a first apex to form a first sector image comprising a plurality of image intensities, transmitting and receiving from at least one other apex of the transducer a plurality of ultrasound beams to form at least one other sector image comprising a plurality of image intensities overlapping a portion of the first sector image to form an overlap region, and combining the first sector image and the at least one other sector image to produce a compound image.

37 Claims, 15 Drawing Sheets

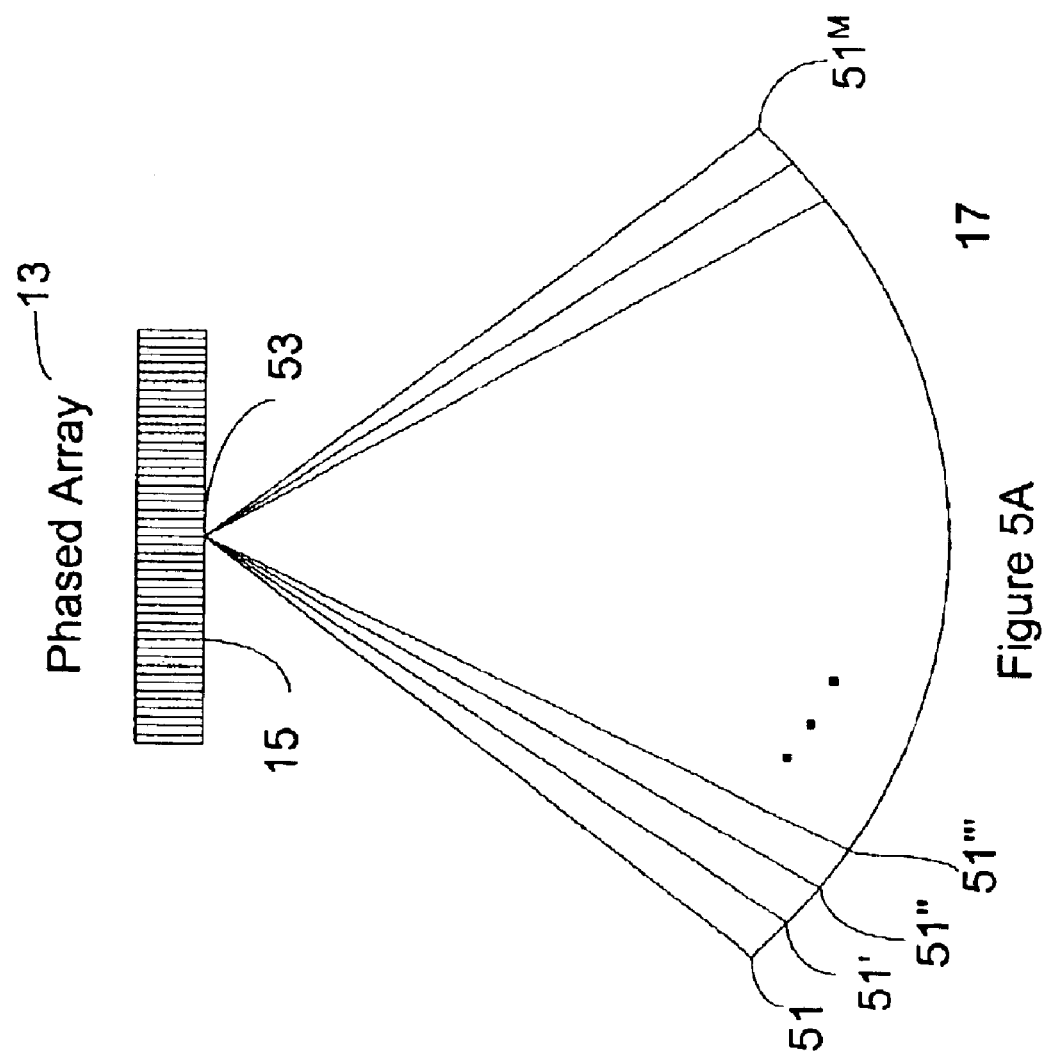

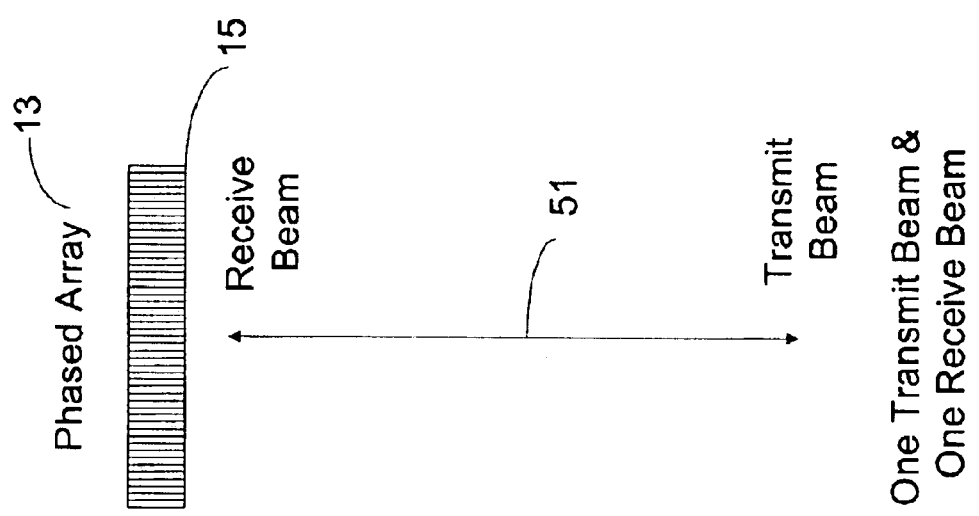

METHOD AND APPARATUS FOR ULTRASOUND DIAGNOSTIC IMAGING

BACKGROUND OF THE INVENTION

1. Field of the Invention

The present invention relates to a method and apparatus for reducing speckle noise in phased array images. Specifically, the present invention teaches the incoherent compounding of multiple sector images formed from multiple apex positions to produce a phased array image with reduced noise.

2. Description of Related Art

Ultrasound imaging has been widely used in diagnosis of diseases in organs, such as heart, liver, kidney, breast, prostate, thyroid, fetus, blood vessels and others. For example, ultrasound imaging can discern tumors from healthy tissues by subtle difference in the brightness and/or shape of an image. The ultrasound signal scattered from the body contains speckle noise patterns due to interference between multiple echo signals from multiple scatterers in the imaging area. Ultrasound tissue images or B-mode images are especially affected by speckles noise or patterns. This noise is very annoying and overrides on a real image of structures, resulting in lower contrast between the image of the structure and the background. In clinical conditions, the speckle noise can cause the detection of small tumor difficult and thus is a problem.

What is therefore needed is an apparatus and method for using the apparatus to reduce speckle noise in ultrasound images.

SUMMARY OF THE INVENTION

Accordingly, it is an object of the present invention to provide a method and apparatus for reducing speckle noise in phased array images.

In accordance with the present invention, a method for reducing noise in ultrasound images comprises the steps of transmitting and receiving from an ultrasound transducer comprising a plurality of apexes a plurality of ultrasound beams from a first apex to form a first sector image comprising a plurality of image intensities, transmitting and receiving from at least one other apex of the transducer a plurality of ultrasound beams to form at least one other sector image comprising a plurality of image intensities overlapping a portion of the first sector image to form an overlap region, and combining the first sector image and the at least one other sector image to produce a compound image.

In accordance with the present invention, a method for reducing noise in ultrasound images comprises the steps of transmitting and receiving from an ultrasound transducer comprising a first and second apex a plurality of ultrasound beams from the first apex to form a first sector image comprising a plurality of image intensities, transmitting and receiving from the second apex a plurality of ultrasound beams to form a second sector image comprising a plurality of image intensities overlapping a portion of the first sector image to form an overlap region, and combining the first sector image and the second sector image to produce a compound image.

In accordance with the present invention, an apparatus for reducing noise in ultrasound images comprises an ultrasound transducer comprising a transmitter and a receiver the transducer comprising a plurality of apexes adapted to transmit and receive a plurality of ultrasound beams from a first apex forming a first sector image comprising a plurality of image intensities the transducer further adapted to transmit and receive a plurality of ultrasound beams from an apex different from the first apex to form at least one other sector image comprising a plurality of image intensities overlapping a portion of the first sector image to form an overlap region, and means for combining the first sector image and the at least one other sector image to produce a compound image.

BRIEF DESCRIPTION OF THE DRAWINGS

FIG. 5A A diagram of a plurality of ultrasound beams used to form a sector image of the present invention.

FIG. 5C A diagram of the single transmit and receive configuration of the present invention.

DETAILED DESCRIPTION OF THE PREFERRED EMBODIMENT(S)

It is therefore a central aspect of the present invention to reduce speckle noise arising in phased array imaging by incoherently adding (compounding) multiple sector images from multiple apex positions.

Figure 1:
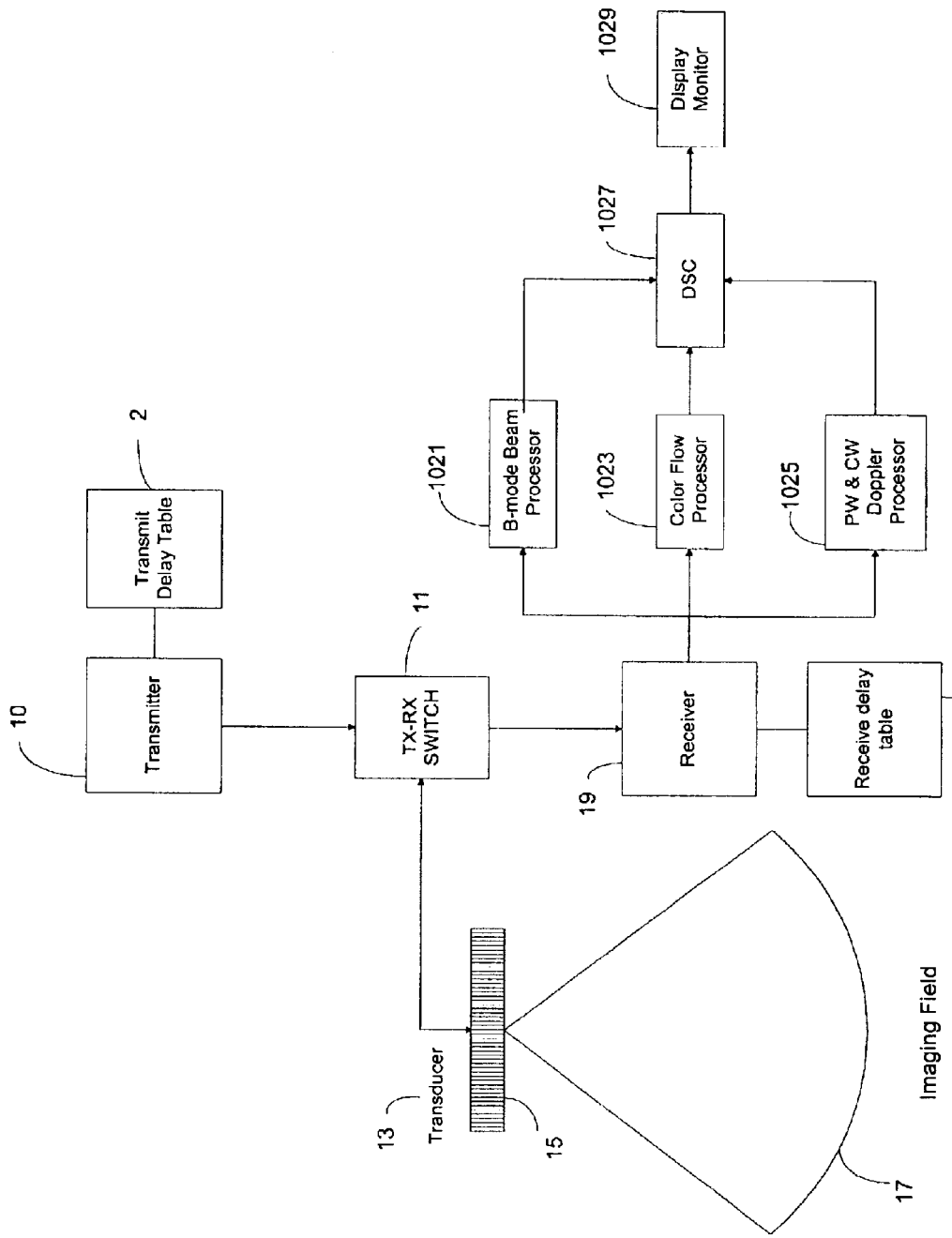
FIG. 1 A diagram of an ultrasound imaging system of the present invention.

With reference to FIG. 1, there is illustrated a block diagram of an ultrasound system 1. Upon a command from the ultrasound system's computer (not shown), transmitter (including transmit beamformer) 10 sends electrical signals of L channels (typically 48 to 128 channels) to the phased array transducer 13 comprised of multiple (or typically 48 to 128) elements 15 through transmit/receive (TX-RX) switch 11. The transducer element pitch (distance between 2 adjacent elements) is generally half (0.5) (or between 0.4 and 0.6) wavelength of the ultrasound frequency, (e.g. about 0.15 mm for 3.5 MHz). These signals are appropriately delayed by the transmit beamformer (not shown) in the transmitter 10 so that ultrasound signals are accurately steered and focused. Ultrasound is transmitted into a part of a body forming the ultrasound imaging field 17 to be imaged and scattered back to the phased array transducer 13. The phased array transducer 13 receives scattered ultrasound signals and converts the received ultrasound signals to electrical signals. The L-channel signals are then received by the receiver 19.

Figure 2:
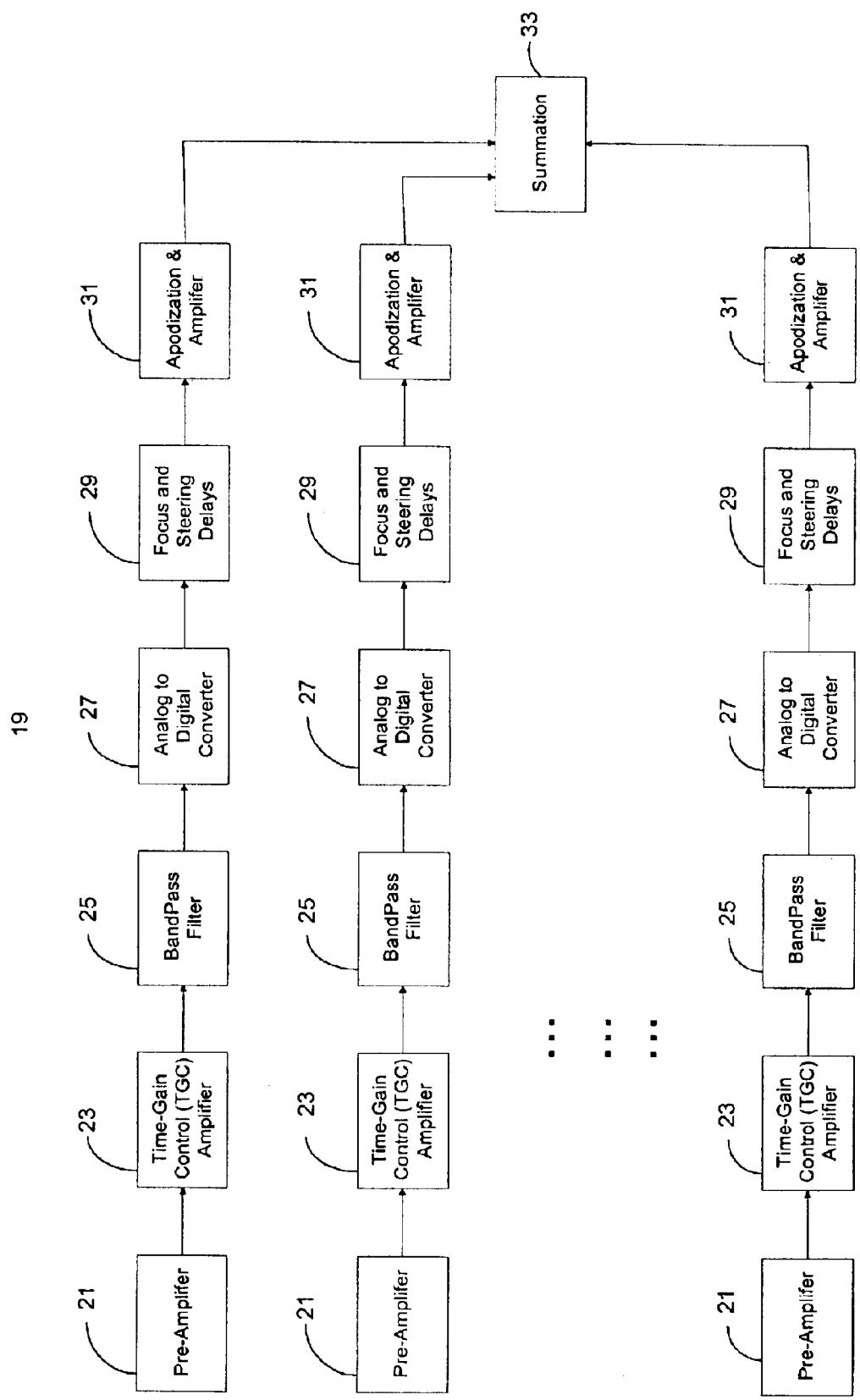
FIG. 2 A block diagram of the receive beamformer of the present invention.

With reference to FIG. 2, there is illustrated in detail the receiver 19, or receive beamformer. Receiver 19 consists of pre-amplifiers 21, time-gain control amplifiers 23, bandpass filters 25, analog-to-digital converters 27, delays and/or phase shifters 29, apodization amplifiers 31, and a summation element 33. The received signals are pre-amplified and time-gain controlled to account for attenuation in tissues, bandpass filtered to remove noise and then beamformed by adding delays to each channel signal for focusing and steering and summing all channels signals with correct delays.

With continued reference to FIG. 1, the beamformed signal is output from the receiver 19 and goes through postprocessing, namely, B-mode beam processing by B-mode beam processor 1021, blood flow imaging by color flow processor 1023, and blood velocity spectrum processing by pulse-wave (PW) Doppler processor or continuous-wave (CW) Doppler processor 1025. These B-mode and color flow beam signals as well as the Doppler velocity spectrum are scan-converted by digital scan converter (DSC) 1027 to be displayed on display monitor 1029 as an image.

Figure 3:
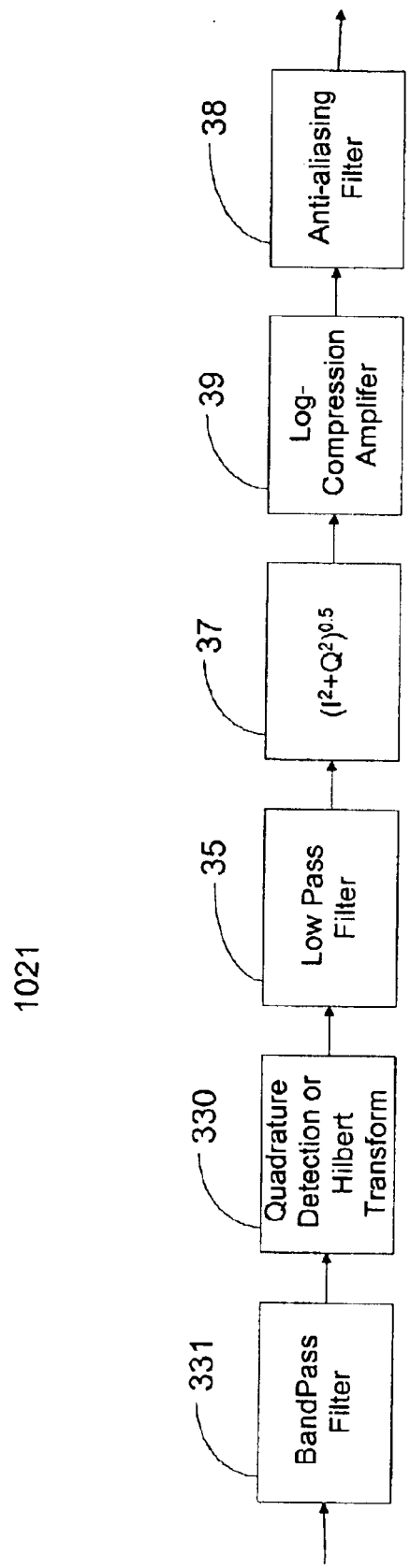
FIG. 3 A block diagram of the B-mode beam processor of the present invention.

With reference to FIG. 3, there is illustrated the B-mode beam processor 1021 of the present invention. B-mode beam processor 1021 consists of a bandpass filter 331, a quadrature detection or Hilbert Transform element 330, a low pass filter 35, a square rooter or $(I^2+Q^2)^{0.5}$ (I: In-phase signal; Q: Quadrature signal) 37, a log-compression amplifier 39, and an anti-aliasing filter 38.

Figure 4:
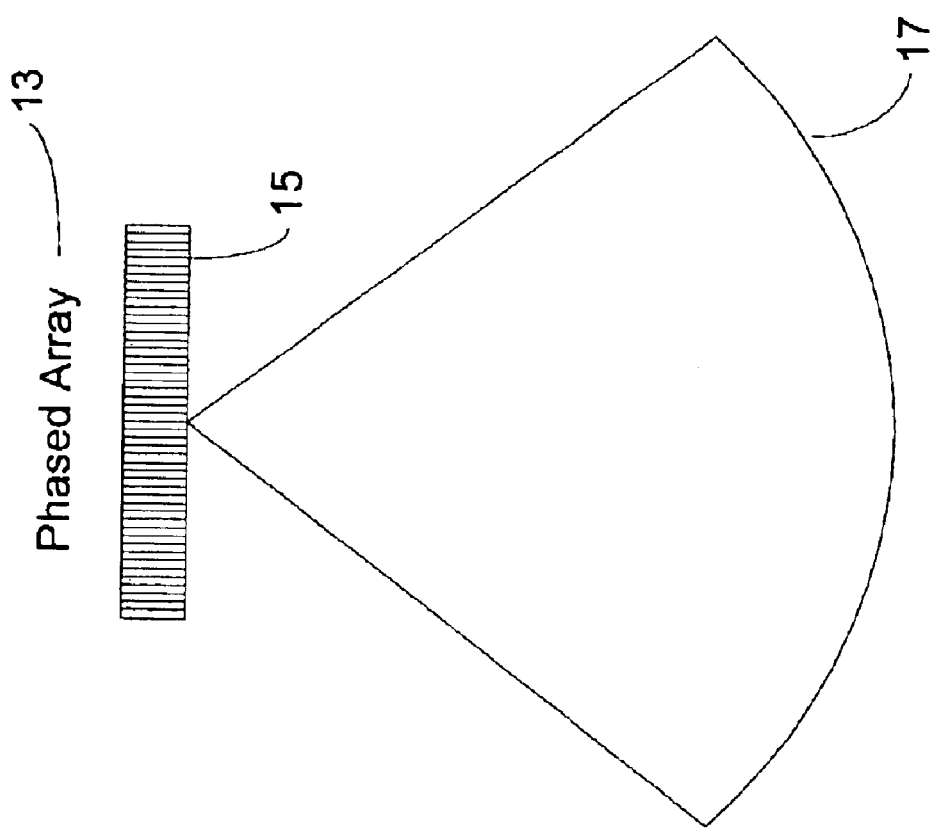
FIG. 4 A diagram of a sector image of the present invention.
Figure 5B:
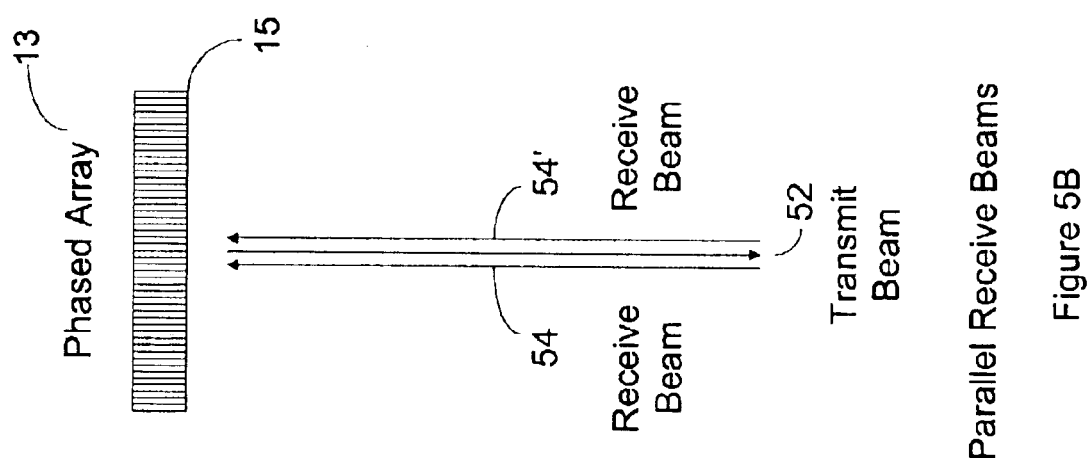
FIG. 5B A diagram of the parallel beam transmit and receive configuration of the present invention.

With reference to FIG. 4, there is illustrated a sector image 17 format in which phased array transducer 13 imaging is generally performed. In the sector, the transmission and reception of ultrasound beams are usually performed in sequence as shown in FIG. 5A. For example, beam 51 is transmitted and received in the left corner of the sector. Next, ultrasound beam 51' is transmitted and received adjacent to beam 51. Ultrasound beam 51" and ultrasound beam 51''' follow as shown. This sequence continues until the right corner is reached by ultrasound beam $\mathbf{51}^M$. Alternatively, beams can be interleaved or other beam sequences can be performed. In the above discussion only one ultrasound beam 51 is received per one transmit ultrasound beam as illustrated in FIG. 5C. However, more than one ultrasound beam can be received for one transmit beam to increase frame rate, spatial resolution or ultrasound beam density. For example, 2 ultrasound beams 54, 54' can be simultaneously received or formed per one transmitted beam 52 by applying appropriate receive time delays in parallel receive channels as illustrated in FIG. 5B. Furthermore, 4 ultrasound beams can be simultaneously received or formed per one transmitted ultrasound beam. The number of receive beams per transmit beam can be further increased to 8, 16 or more. Although the simultaneous receive beam technique requires parallel receive processing, or parallel beam processing, it can increase frame rate by a factor of the number of receive beams per transmit beam. This is called parallel receive processing or the parallel receive beam technique. A sector image 17 with an apex 53 in the center of the phased array transducer 13 is created by processing these received ultrasound beams (51, 51', 51" ... $\mathbf{51}^M$) or signals by the receiver 19, B-mode beam processor 1021 and digital scan converter (DSC) 1027.

Figure 6:
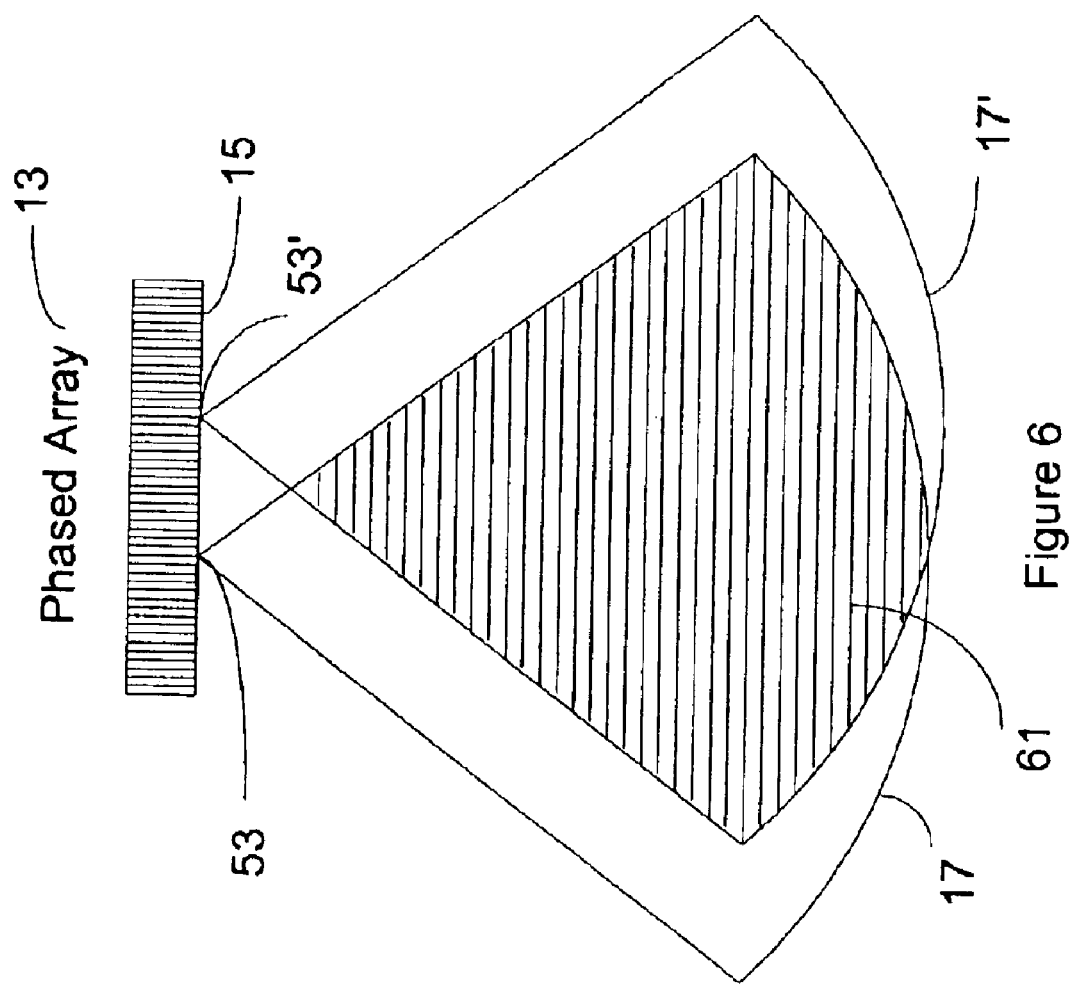
FIG. 6 A diagram of an overlapping region formed by two sector images of the present invention.
Figure 13:
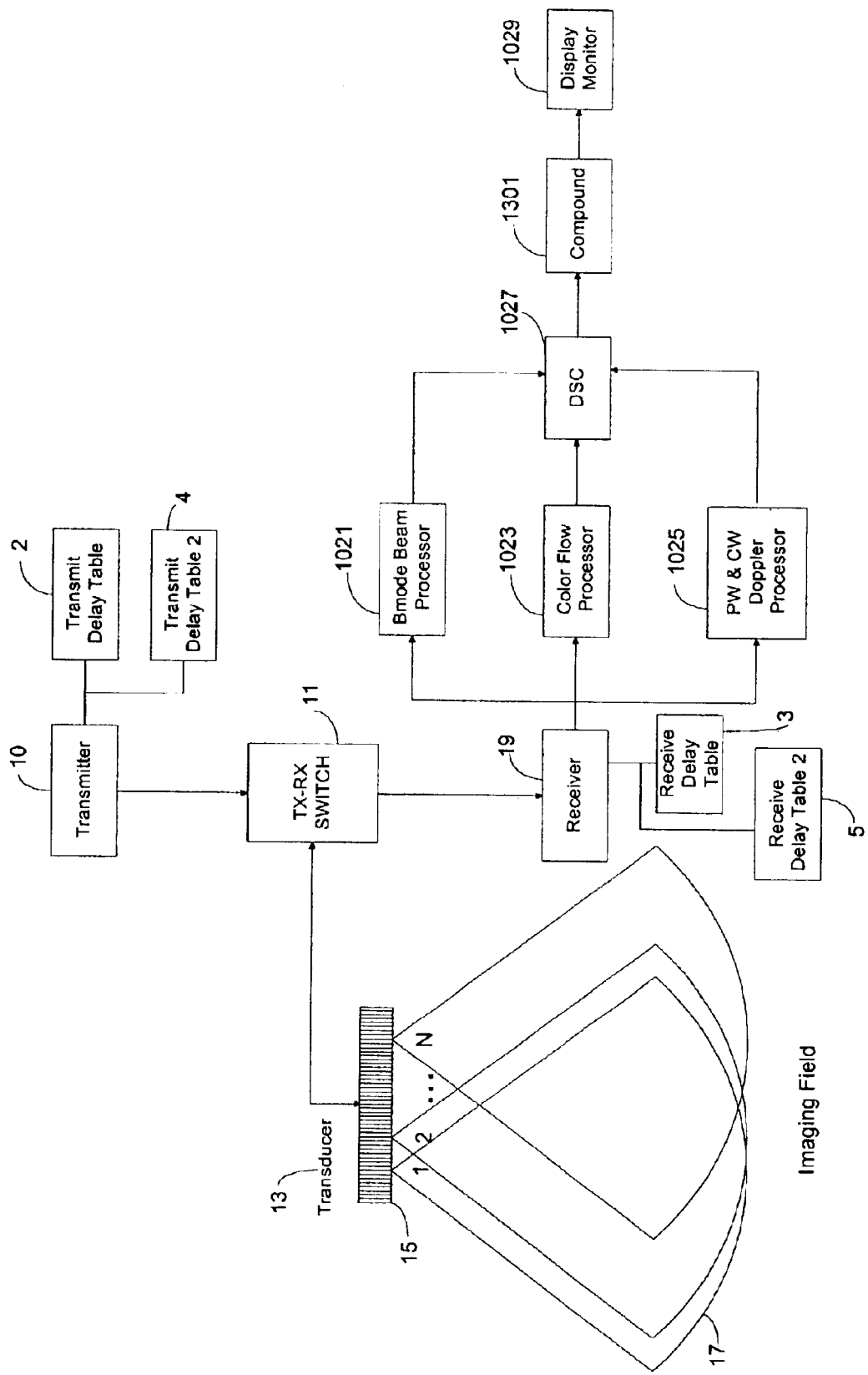
FIG. 13 A diagram of an ultrasound imaging system of the present invention showing the compounding unit.

With reference to FIG. 6, there is illustrated two overlapping sector images 17, 17' each with a different apex 53, 53'. Ultrasound beams are transmitted and received for each sector as stated previously. To be specific, ultrasound beams are transmitted by transmitter 10 with a set (i.e. for L channels) of time delays for beam steering and focusing and received by receiver 19 with another set of time delays for beam steering and focusing from sector apex 53. Then sector apex moves to 53' and ultrasound beams are transmitted with another set of time delays for steering and focusing and received with another set of time delays for steering and focusing from apex 53'. Prior to imaging, these sets of time delays are generated and stored in transmit delay table 2 and associated memory 4 and receive delay table 3 and associated memory 5 as illustrated in FIG. 13. The additional sets of time delays for sector image at 53' are stored in memories 4 and 5. Time delays for one sector image at one sector apex are normally stored in transmit delay table 2 and receive delay table 3. Furthermore, additional memories (or transmit and receive delay tables) 4, 5 are used to store additional sets of time delays for additional sector images at additional sector apexes. Two sector images 17, 17' are created by processing the received ultrasound beams or signals in the receiver, B-mode beam processor and digital scan converter (DSC) and temporally stored in memories contained in an image compounding unit 1301 as disclosed in FIGS. 7 and 13 and discussed below. In the center region of the imaging field, the two sector images overlap each other to form a compound image at overlap region 61.

Figure 7:
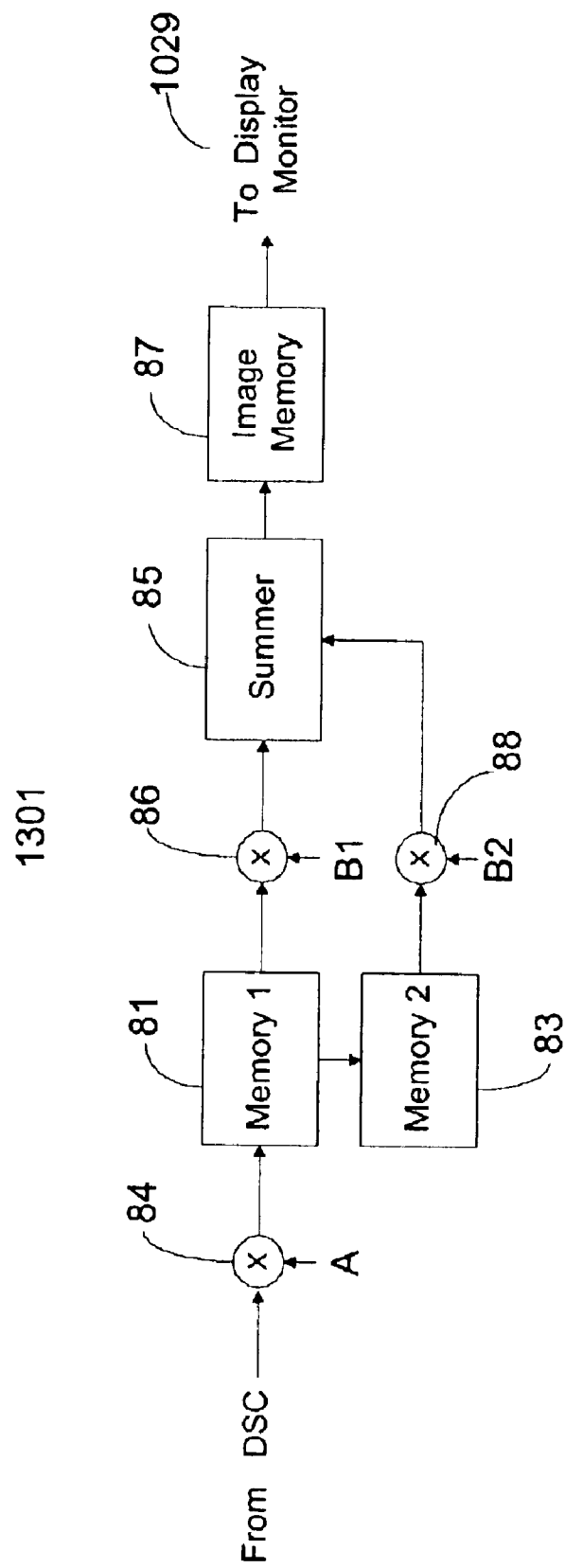
FIG. 7 A block diagram of a preferred embodiment of an apparatus for combining two sector images of the present invention.

The details of a preferred embodiment of the memory unit and addition (summation) unit comprising imaging compounding unit 1301 employed are illustrated with reference to FIG. 7. After an image from the first apex 53 position is created, it is stored in first memory 81 after multiplying, via a multiplier 84, a weight coefficient A which varies from one image to another to account for image sensitivity difference and to equalize overall image sensitivity due to apex positions. Next, an image from the second apex 53' is created and sent to the first memory 81 after the first image from the first apex 53 position stored in the first memory 81 is passed onto the second memory 83. Images from two different apex positions in memories 81, 83 are multiplied by multipliers 86, 88, with coefficients of B1, B2, respectively, and are summed by the summer 85. B1 and B2 are spatially dependent. In other words, B1 can vary from one point to another in an image. B2 can also vary from one point to another. In the overlap region 61 of FIG. 6, B1 and B2 are both 0.5. In the other areas, B1 and B2 are both 1.0. The two sector images are thus compounded or added with the appropriate weight coefficients to create uniform overall brightness and a compounded image is outputted to image memory 87 and displayed in display monitor 1029. Weight coefficients other than equal weights can be used to selectively weigh sectors images 17, 17', etc. For example, in the overlap region 61 of FIG. 6, B1 can be chosen to be 0.7 while B2 can be chosen to be 0.3 to put more weight on the image in memory 81. These coefficients are chosen so that the sum of coefficients at any given image point becomes 1.0 to make the overall image brightness uniform. The ultrasound system can display either only the compounded image in the center area (shaded) 61 or the whole image including the uncompounded areas as shown in FIG. 6 by using the weight coefficients B1 and B2 of 0 in the areas not to be displayed.

Figure 8:
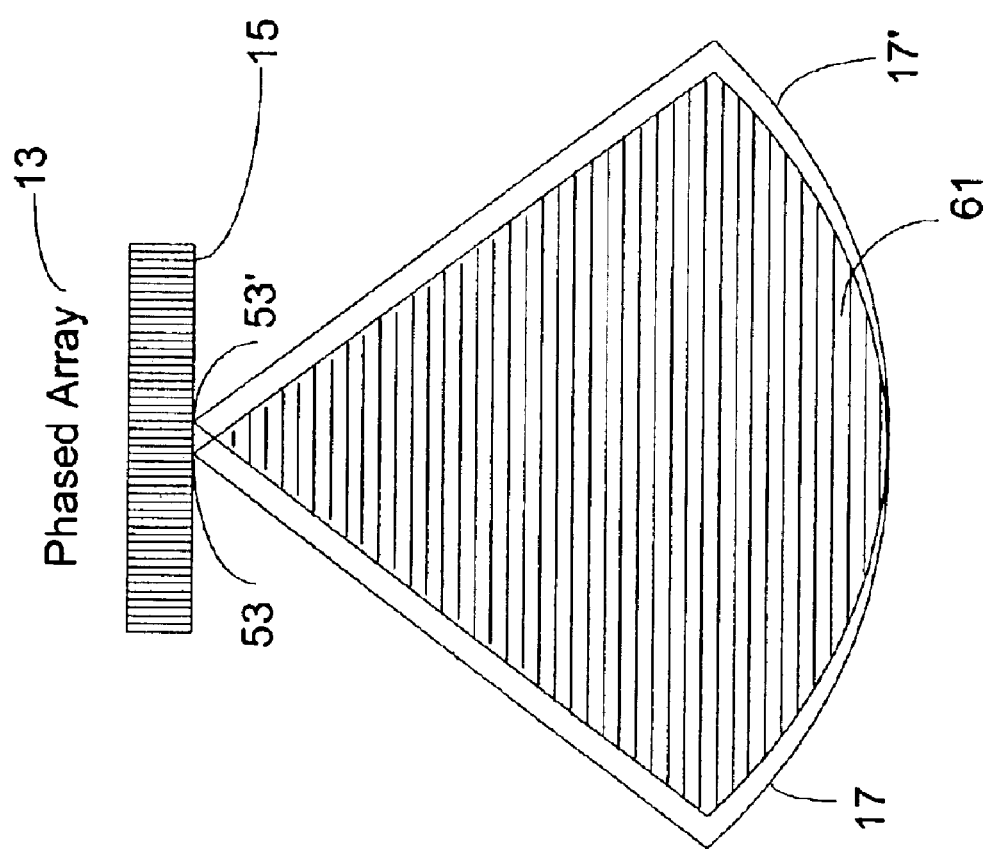
FIG. 8 A diagram of an overlapping region formed by two sector images with nearly adjacent apexes of the present invention.
Figure 9:
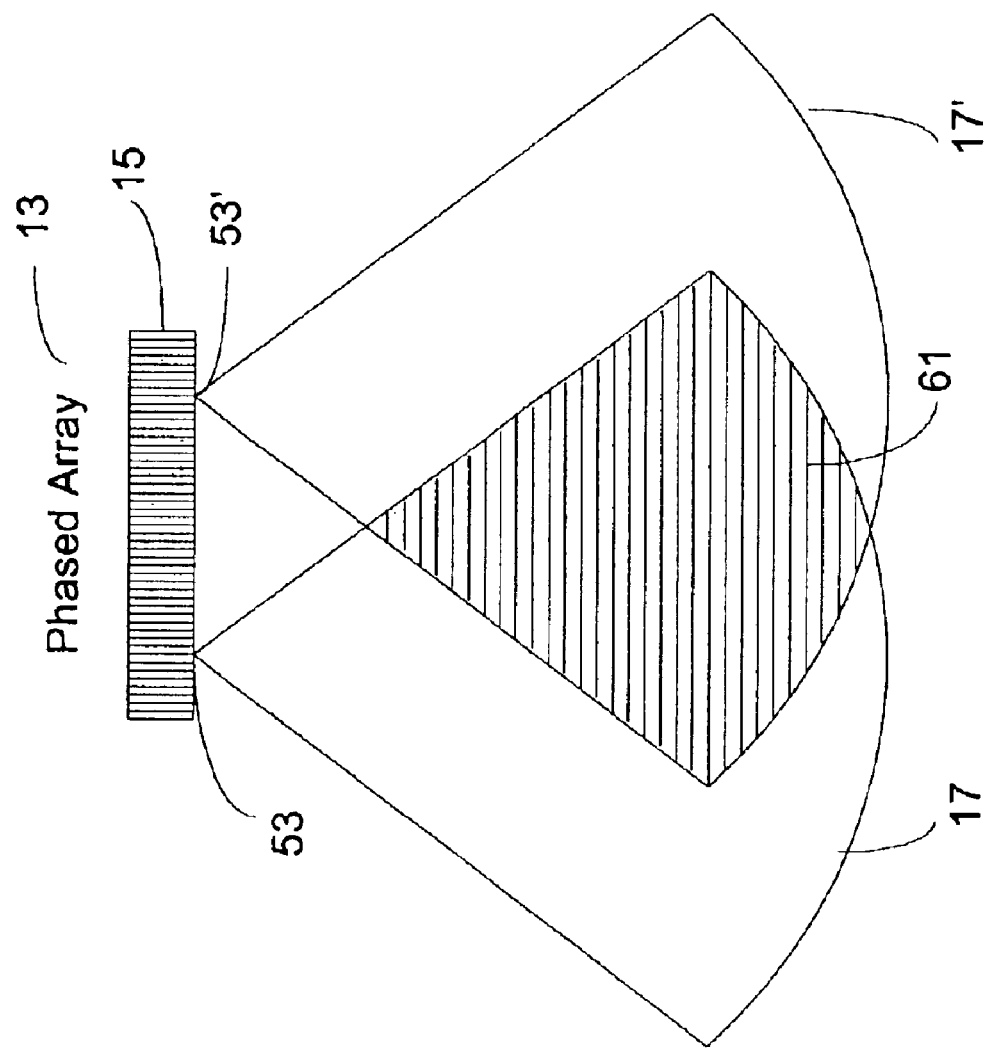
FIG. 9 A diagram of an overlapping region formed by two sector images with widely separated apexes of the present invention.

As is illustrated with reference to FIG. 8, the distance between the apex positions 53, 53' can be as small as several elements 15 in width. In fact, the distance can be as small as half a transducer element's 15 pitch. Alternatively, the distance can be very large as shown with reference to FIG. 9. The distance can be as large so as to approximate the width of the entire phased array transducer 13. As described previously, apex positions alternate so that the last two individual sector images before compounding are always created at two different apex positions. In other words, the apex position moves from 53 to 53' and returns back to 53 and 53' and so on. Or the apex position moves from 53 to 53',53, 53', 53, 53' . . .

The compounded B-mode (or greyscale) tissue image can be combined with a color flow image to create a composite image of tissue and blood flow. In addition, pulse wave (PW) or continuous wave (CW) Doppler spectrum can be used to measure blood flow velocity and can be combined with the compounded B-mode tissue image with or without the color blood flow image.

Figure 10:
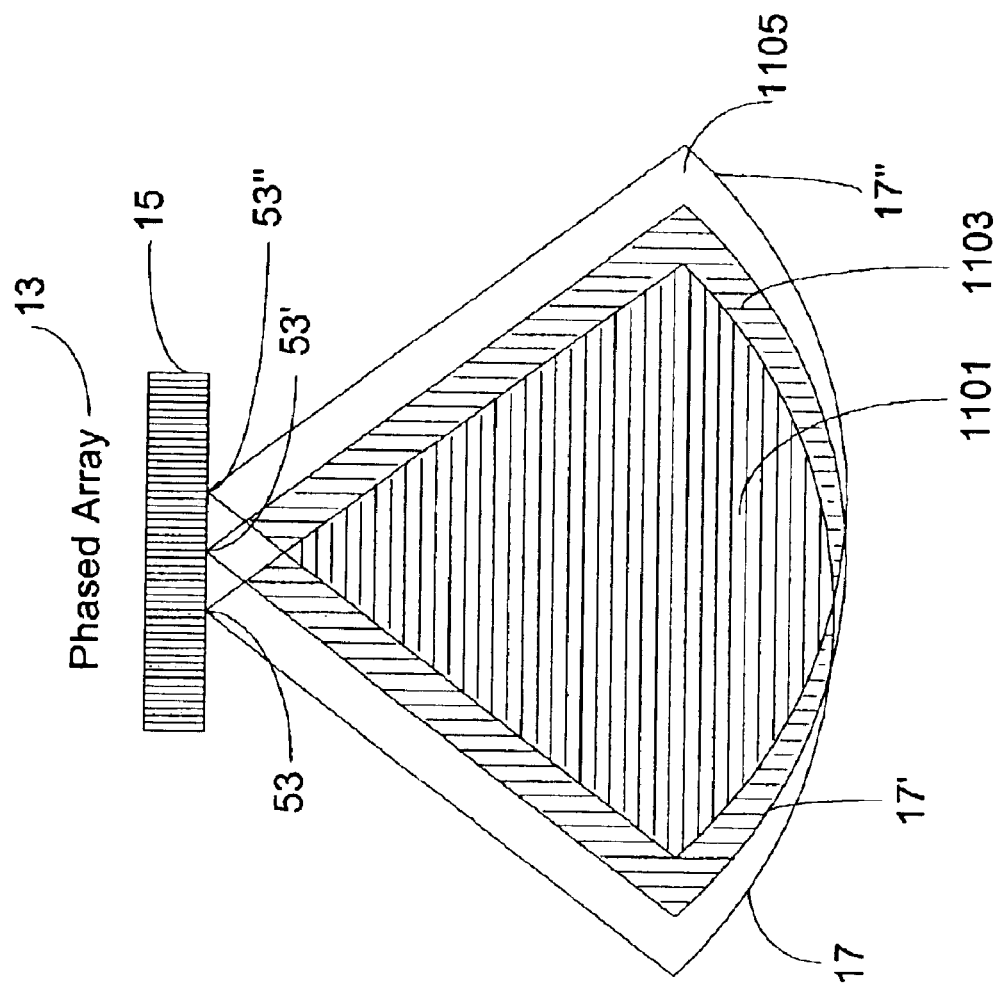
FIG. 10 A diagram of overlapping regions formed by three sector images of the present invention.

Image compounding can be further enhanced by additional sector images as illustrated with reference to FIG. 10. Three sector images 17, 17', 17" are shown with a corresponding three different apex positions 53, 53', 53". The apex position moves from 53 to 53' and 53" and returns back to 53, 53' 53" and so on. Or the apex position moves from 53 to 53', 53", 53, 53', 53", . . .

Figure 11:
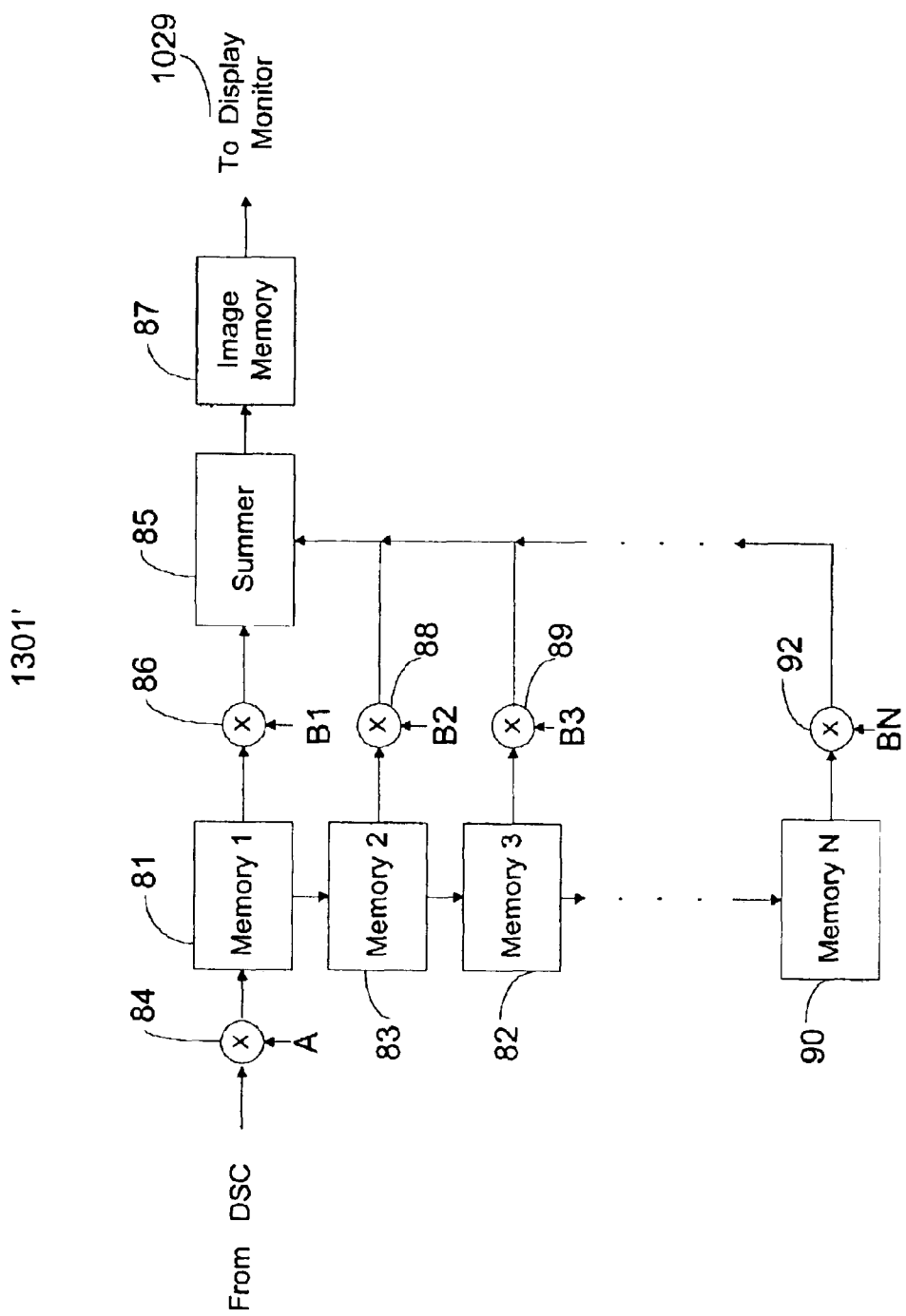
FIG. 11 A block diagram of a preferred embodiment of an apparatus for combining multiple sector images of the present invention.

By adding more sectors, speckle patterns and image artifacts are more greatly reduced, resulting in better image uniformity and higher image contrast of more use in clinical diagnosis. In FIG. 10, ultrasound beams are transmitted and received for each sector as stated previously. Three sector images 17, 17', 17'" are individually created by processing the received ultrasound beams or signals in the receiver 19, B-mode beam processor and digital scan converter (DSC) 1027 and temporally stored in memories 81, 83, 82 . . . as illustrated with reference to FIG. 11. With continued reference to FIG. 10, in the center regions 1101 and 1103 of the imaging field, two or three sector images 17, 17', 17" override each other and image compounding is possible in this area. With continued reference to FIG. 11, there is shown in block diagram form the compounding of N images (i.e., N=3 for the case illustrated in FIG. 10). Three sector images are first multiplied by weight coefficient A, which varies from one image to another to equalize image sensitivity due to apex positions and are temporally stored in memories (1–3) 81, 83, 82. Images from three different apex positions in memories 81, 83, 82 are multiplied by multipliers 86, 88, 89 with coefficients of B1, B2, B3, respectively, and summed by the summer 85. The coefficients B1, B2, B3 are all spatially dependent. In other words, B1 can vary from one point to another in an image. B2 and B3 each can also vary from one point to another in an image. In the most central area (1101), B1, B2, and B3 are ⅓ (or 0.333) each. In the next central areas (1103), B1, B2 and B3 are ½ (0.5) each. In all other areas 1105, B1, B2 and B3 are all 1.0 each. In other words, the coefficients are 1/J where J is the number of images overridden in the area. The three sector images are thus compounded or added with appropriate weight coefficients to create uniform overall brightness and a compounded image is outputted to image memory 87 and displayed in display monitor 1029. Other weight coefficients can be used to selectively weigh the sector images. However, the sum of all coefficients (B1, B2, B3) will be 1.0 at any given point in an image. The ultrasound system can display either only the most central area 1101, the center areas 1103, or the whole areas including no compound areas 1105 by masking areas by using the weight coefficients of 0 in the areas the user doesn't want to show. The distance between two adjacent apex positions can vary from a very small one (as small as ½ transducer element pitch) to a very large one (approximately the size of the whole transducer). The distance between apexes 53 and 53' can be either equal to or different from the distance between apexes 53' and 53". In addition, three apex positions can change in time sequence so that the last three sector images are created at three different apex positions and can be compounded as discussed above. The compounded B-mode (or greyscale) tissue image can be combined with a color flow image to create a composite image of tissue and blood flow. In addition, pulse wave (PW) or continuous wave (CW) Doppler spectrum can be used to measure blood flow velocity and can be combined with the compounded B-mode tissue image with or without the color blood flow image. In an alternative embodiment, the compounding apparatus shown in FIG. 11 can be implemented by digital signal processor(s) (DSP) and memories. Furthermore, the parallel receive beam technique can be added to increase frame rate, spatial resolution or the ultrasound beam density.

Figure 12:
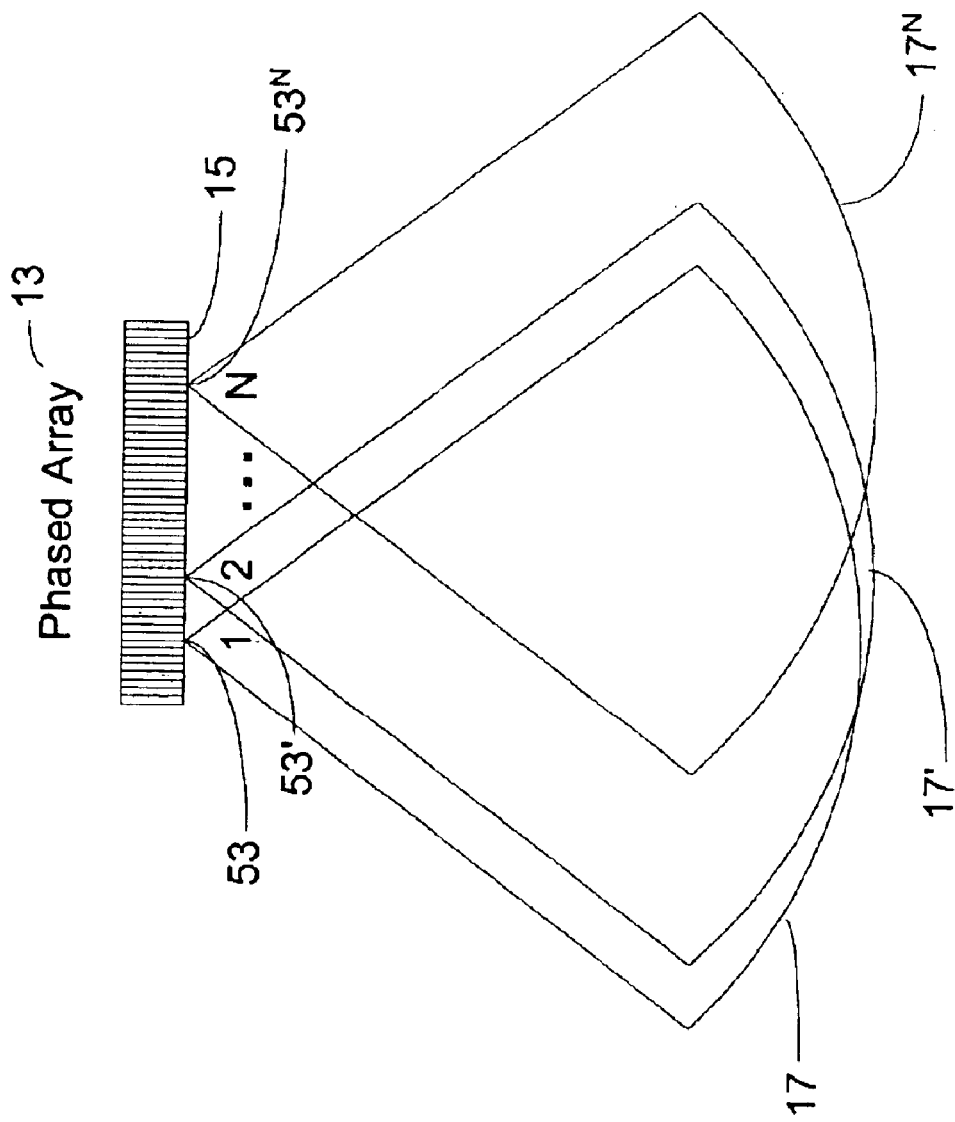
FIG. 12 A diagram of overlapping regions formed by multiple sector images of the present invention.

Image compounding can be further enhanced by additional sector images as shown in FIG. 12 in which N sectors are shown with N different apex positions 53, 53', $53^N$. The apex position moves from 53 to 53' . . . $53^N$ and returns back to 53, 53' . . . $53^N$ and so on. In other words, the apex position moves from 53 to 53', . . . $53^N$, 53, 53' . . . $53^N$, 53, 53' . . .

As in the previous section, by adding more sectors, speckle patterns and image artifacts are reduced, resulting in better image uniformity and higher image contrast and therefore are more useful in clinical diagnosis. Ultrasound beams are transmitted and received for each sector 17, 17', . . . $17^N$ as stated previously. N sector images are individually created by processing the received ultrasound beams or signals in the receiver 19, B-mode beam processor 1021 and digital scan converter (DSC) 1027 and appropriately multiplied by weight coefficient A, which varies from an image to another to equalize image sensitivity due to apex positions and temporally stored in memories 81, 83, 82, . . . 90 in FIG. 11. In the center region of the imaging field, multiple sector images override each other and image compounding is possible in this area. Images from N different apex positions in memories 81, 83, 82, . . . 90 are multiplied by multipliers 86, 88, 89, . . . 92 with coefficients of B1, B2, B3, . . . BN, respectively, and summed by the summer 85. The most central area in which N sectors override, the weight coefficients, B1, B2 . . . BN, which are spatially dependent, are 1/N for equal weight for all sector images. A next central area in which N−1 sectors override, the weight coefficients, B1, B2 . . . BN will be 1/(N−1) for equal weight compounding. All weight coefficients will be 1/J or an inverse of the number (J) of sectors Which override in this area for equal weight. The multiple sector images are thus compounded or added by the summer 85 with appropriate weight coefficients to create uniform overall brightness and a compounded image is outputted to image memory 87 and displayed in display monitor 1029. Other weight coefficients can be chosen to selectively weigh some sector images. However, the sum of all coefficients (i.e., B1, B2, . . . BN) will be 1.0 at any given point in an image. The ultrasound system can display either only the center areas or the whole areas including no compound areas by masking areas by using the weight coefficients of 0 in the areas which the user doesn't want to show. The distance between two adjacent apex positions can vary from a very small one (as small as ½ transducer element pitch) to a very large one (the size of the whole transducer). The distance between any two adjacent apexes (e.g. 53 and 53') can be either equal to or different from the distance between any other two adjacent apexes (e.g. 53' and 53"). In addition, N apex positions can change in sequence so that the last N sector images were always created at N different apex positions and can be compounded as discussed above. The compounded B-mode (or greyscale) tissue image can be displayed alone or combined with a color flow image to create a composite image of tissue and blood flow. In addition, pulse wave (PW) or continuous wave (CW) Doppler spectrum can be used to measure blood flow velocity and can be combined with the compounded B-mode tissue image with or without the color blood flow image. Furthermore, the parallel receive beam technique can be added to increase frame rate, spatial resolution or the ultrasound beam density.

It is apparent that there has been provided in accordance with the present invention a method of incoherently compounding multiple sector images formed from multiple apex positions to produce a phased array image with reduced noise which fully satisfies the objects, means, and advantages set forth previously herein. Specifically, it is contemplated that one could combine any number of techniques disclosed herein, such as parallel beam reception, to further satisfy the object of the present invention. While the present invention has been described in the context of specific embodiments thereof, other alternatives, modifications, and variations will become apparent to those skilled in the art having read the foregoing description. Accordingly, it is intended to embrace those alternatives, modifications, and variations as fall within the broad scope of the appended claims.

What is claimed is:

1. A method for reducing noise in ultrasound images comprising the steps of:
   transmitting and receiving from an ultrasound transducer comprising a plurality of apexes a plurality of ultrasound beams from a first apex to form a first sector image comprising a plurality of image intensities;
   transmitting and receiving from at least one other apex of said transducer a plurality of ultrasound beams to form at least one other sector image comprising a plurality of image intensities overlapping a portion of said first sector image to form an overlap region; and
   combining said first sector image and said at least one other sector image to produce a compound image.

2. The method of claim 1 wherein said transmitting and receiving said plurality of ultrasound beams from a first apex occurs prior to transmitting and receiving said plurality of ultrasound beams from said at least one other apex.

3. The method of claim 1 comprising the additional steps of:
   creating and storing in a transmit delay table a plurality of time delays;
   creating and storing in a receive delay table a plurality of time delays; and
   performing said transmitting and receiving from said plurality of apexes in accordance with said plurality of time delays stored in said transmit delay table and said receive delay table multiple times.

4. The method of claim 1 wherein said step of combining said first sector image and said at least one other sector image to produce a compound image comprises the additional steps of:
   multiplying each of said plurality of image intensities comprising said first sector image and each of said at least one other sector images by a coefficient equal to 1/J where J is a number of sector images overlapping at a location occupied by each of said plurality of image intensities.

5. The method of claim 1 wherein said step of combining said first sector image and said at least one other sector image to produce a compound image comprises the additional steps of:
   defining a plurality of overlap regions each comprising an integer number of said plurality of sector images overlapping within each of said plurality of overlap regions;
   multiplying each of said plurality of sector images comprising each of said plurality of overlap regions by a corresponding coefficient.

6. The method of claim 5 wherein said plurality of coefficients corresponding to each of said plurality of sector images forming one of said overlapping regions sum to 1.0.

7. The method of claim 6 wherein multiplying each of said plurality of overlap regions by a corresponding coefficient comprises multiplying at least one of said overlap regions by zero.

8. The method of claim 1 comprising the additional step of multiplying each of said plurality of image intensities forming one of said sector images by a weight coefficient.

9. The method of claim 1 comprising the additional step of ensuring that each of said at least one other sector image is formed from an apex different from an apex from which an immediately preceding one of said at least one other sector image is formed.

10. The method of claim 1 wherein said step of transmitting and receiving from at least one other apex comprises said at least one other apex located at least one-half of a transducer element's pitch from said first apex.

11. The method of claim 1 wherein said step of combining said first sector image and said at least one other sector image to produce a compound image comprises producing a B-mode tissue image.

12. The method of claim 1 further comprising the additional step of combining said compound image with a color blood flow image.

13. The method of claim 1 further comprising the additional step of combining said compound image with a blood flow velocity spectrum image selected from the group consisting of pulse wave (PW) and continuous wave (CW) Doppler spectrum.

14. The method of claim 1 further comprising the additional step combining said compound image with a blood flow velocity spectrum image and a color blood flow image.

15. The method of claim 1 wherein said combining step comprises combining said images using a digital signal processor and at least one memory unit.

16. The method of claim 1 wherein said combining said first sector image and said at least one other sector image to produce said compound image comprises the steps of:
   multiplying each of said plurality of image intensities comprising each of said plurality of sector images stored on each of said plurality of memory units by a weight coefficient;
   storing each of said plurality of sector images in a memory unit;
   multiplying at least a portion of each of said plurality of stored sector images by a corresponding coefficient;
   summing each of said portions of said plurality of stored sector images multiplied by said corresponding coefficient and outputting a summed image; and
   storing said summed image in an image memory.

17. The method of claim 1 wherein a plurality of said plurality of received ultrasound beams is received for each of said plurality of transmitted ultrasound beams.

18. The method of claim 17 comprising the additional steps of:
creating and storing in a transmit delay table a plurality of time delays;
creating and storing in a receive delay table a plurality of time delays; and
performing said transmitting and receiving from said plurality of apexes in accordance with said plurality of time delays stored in said transmit delay table and said receive delay table multiple times.

19. The method of claim 17 wherein said step of combining said first sector image and said at least one other sector image to produce a compound image comprises the additional steps of:
multiplying each of said plurality of image intensities comprising said first sector image and each of said at least one other sector images by a coefficient equal to 1/J where J is a number of sector images overlapping at a location occupied by each of said plurality of image intensities.

20. The method of claim 17 wherein said step of combining said first sector image and said at least one other sector image to produce a compound image comprises the additional steps of:
defining a plurality of overlap regions each comprising an integer number of said plurality of sector images overlapping within each of said plurality of overlap regions;
multiplying each of said plurality of sector images comprising each of said plurality of overlap regions by a corresponding coefficient.

21. The method of claim 20 wherein said plurality of coefficients corresponding to each of said plurality of sector images forming one of said overlapping regions sum to 1.0.

22. The method of claim 21 wherein multiplying each of said plurality of overlap regions by a corresponding coefficient comprises multiplying at least one of said overlap regions by zero.

23. The method of claim 17 comprising the additional step of multiplying each of said plurality of image intensities forming one of said sector images by a weight coefficient.

24. The method of claim 17 comprising the additional step of ensuring that each of said at least one other sector image is formed from an apex different from an apex from which an immediately preceding one of said at least one other sector image is formed.

25. The method of claim 17 wherein said step of transmitting and receiving from at least one other apex comprises said at least one other apex located at least one-half of a transducer elements pitch from said first apex.

26. The method of claim 17 wherein said step of combining said first sector image and said at least one other sector image to produce a compound image comprises producing a B-mode tissue image.

27. The method of claim 17 further comprising the additional step of combining said compound image with a color blood flow image.

28. The method of claim 17 further comprising the additional step of combining said compound image with a blood flow velocity spectrum image selected from the group consisting of pulse wave (PW) and continuous wave (CW) Doppler spectrum.

29. The method of claim 17 further comprising the additional step combining said compound image with a blood flow velocity spectrum image and a color blood flow image.

30. The method of claim 17 wherein said combining step comprises combining said images using a digital signal processor and at least one memory unit.

31. The method of claim 17 wherein said combining said first sector image and said at least one other sector image to produce said compound image comprises the steps of:
multiplying each of said plurality of image intensities comprising each of said plurality of sector images stored on each of said plurality of memory units by a weight coefficient;
storing each of said plurality of sector images in a memory unit;
multiplying at least a portion of each of said plurality of stored sector images by a corresponding coefficient;
summing each of said portions of said plurality of stored sector images multiplied by said corresponding coefficient and outputting a summed image; and
storing said summed image in an image memory.

32. The method of claim 17 wherein said transmitting and receiving said plurality of ultrasound beams from said first apex occurs prior to transmitting and receiving said plurality of ultrasound beams from said second apex.

33. A method for reducing noise in ultrasound images comprising the steps of:
transmitting and receiving from an ultrasound transducer comprising a first and second apex a plurality of ultrasound beams from said first apex to form a first sector image comprising a plurality of image intensities;
transmitting and receiving from said second apex a plurality of ultrasound beams to form a second sector image comprising a plurality of image intensities overlapping a portion of said first sector image to form an overlap region; and
combining said first sector image and said second sector image to produce a compound image.

34. A method for reducing noise in ultrasound images comprising the steps of:
transmitting and receiving from an ultrasound transducer comprising a first and second apex a plurality of ultrasound beams from said first apex to form a first sector image comprising a plurality of image intensities;
transmitting and receiving from said second apex a plurality of ultrasound beams to form a second sector image comprising a plurality of image intensities overlapping a portion of said first sector image to form an overlap region; and
combining said first sector image and said second sector image to produce a compound image.

35. An apparatus for reducing noise in ultrasound images comprising:
an ultrasound transducer comprising a transmitter and a receiver said transducer comprising a plurality of apexes adapted to transmit and receive a plurality of ultrasound beams from a first apex forming a first sector image comprising a plurality of image intensities said transducer further adapted to transmit and receive a plurality of ultrasound beams from an apex different from said first apex to form at least one other sector image comprising a plurality of image intensities overlapping a portion of said first sector image to form an overlap region; and
means for combining said first sector image and said at least one other sector image to produce a compound image.

36. The apparatus of claim 35 wherein said means for combining said first sector image and said at least one other sector image comprises an image compounding unit comprising:

means for multiplying each of said plurality of image intensities comprising each of said plurality of sector images by a weight coefficient;

a plurality of memory units each adapted to store one of said plurality of sector images;

means for multiplying at least a portion of each of said plurality of stored sector images by a corresponding coefficient;

a summation unit for summing each of said portions of said plurality of stored sector images multiplied by said corresponding coefficient and outputting a summed image; and an image memory for storing said summed image.

37. The apparatus of claim 36 additionally comprising:

a plurality of time delays adapted to be stored in a transmit delay table; and a plurality of time delays adapted to be stored in a receive delay table.

* * * * *